United States Patent [19]

Butturini

[11] Patent Number: 5,084,620
[45] Date of Patent: Jan. 28, 1992

[54] METHOD OF DETECTING PRE-SPOTTING WHEN DISPENSING SAMPLE

[75] Inventor: Randal S. Butturini, Rochester, N.Y.

[73] Assignee: Eastman Kodak Company, Rochester, N.Y.

[21] Appl. No.: 637,416

[22] Filed: Jan. 4, 1991

[51] Int. Cl.[5] .............................................. G01N 21/59
[52] U.S. Cl. ................................ 250/338.5; 250/340; 250/341
[58] Field of Search ............ 250/341, 340, 339, 338.5, 250/343

[56] References Cited

U.S. PATENT DOCUMENTS

| | | |
|---|---|---|
| 4,006,358 | 2/1977 | Howarth .............................. 250/339 |
| 4,243,883 | 1/1981 | Schwarzmann ..................... 250/343 |
| 4,420,566 | 12/1983 | Jessop et al. ........................... 436/46 |
| 4,492,868 | 1/1985 | Jelvestam et al. .................... 250/345 |
| 4,808,824 | 2/1989 | Sinnar ................................... 250/339 |
| 4,879,471 | 11/1989 | Dahlquist ............................. 250/339 |

*Primary Examiner*—Constantine Hannaher
*Attorney, Agent, or Firm*—Dana M. Schmidt

[57] ABSTRACT

A method of detecting pre-spotting is described, comprising meauring the amount of IR light transmitted through a slide test element, using an IR-emitting diode and a photosensitive transistor or photodiode. The amount of transmission is compared against a standard level up until the time when sample dispensing is to commence.

5 Claims, 4 Drawing Sheets

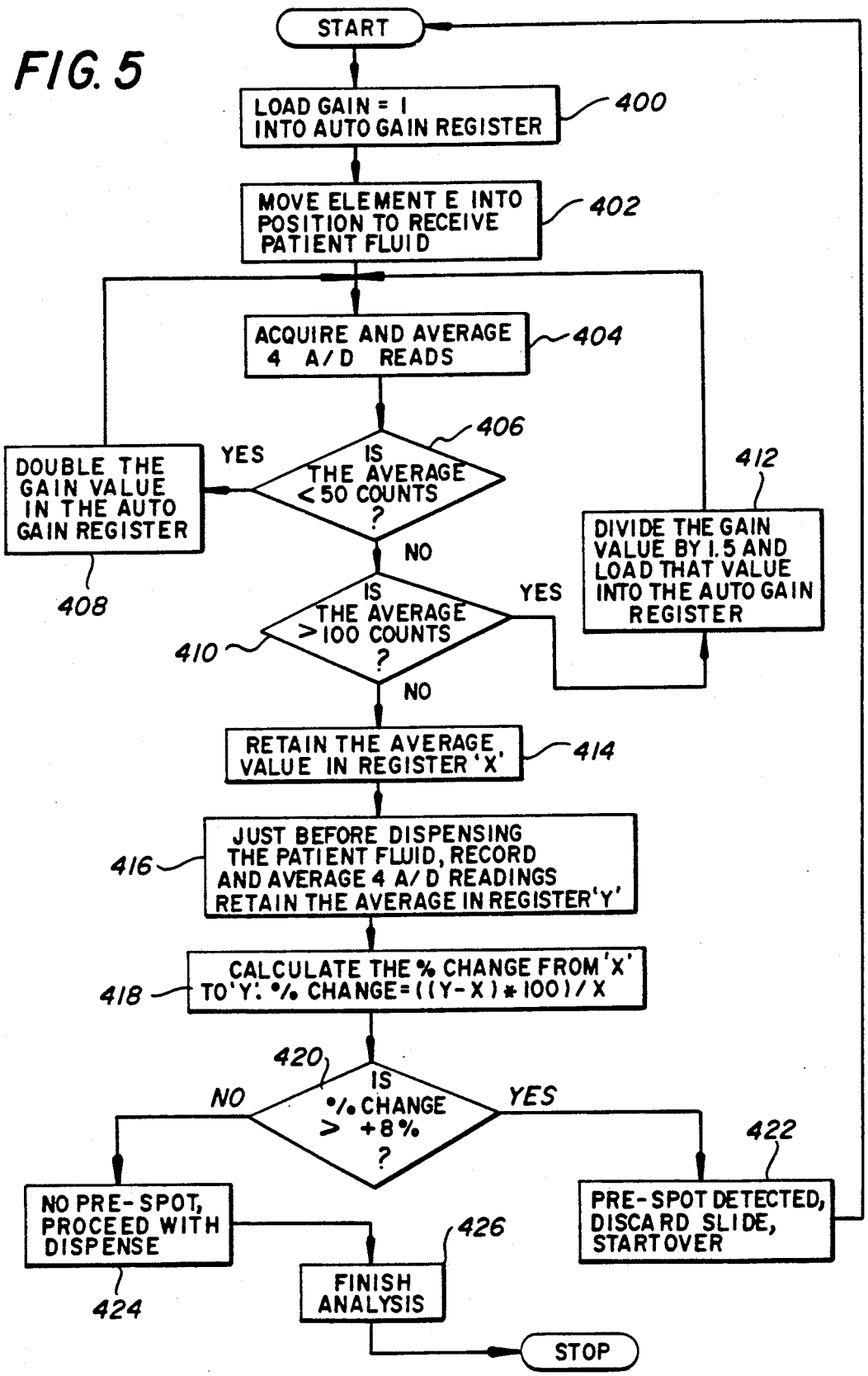

METHOD OF DETECTING PRE-SPOTTING WHEN DISPENSING SAMPLE

FIELD OF THE INVENTION

The invention relates to a method of detecting the undesirable pre-spotting of slide test elements prior to sample dispensing, using improved apparatus.

BACKGROUND OF THE INVENTION

In analyzers of body liquids such as those available from the Eastman Kodak Company under the trademark "Ektachem 700" or "Ektachem 400", it has been conventional to use as part of the analyzer, apparatus for detecting liquid dispensing behavior onto a dried test element, the apparatus comprising an infrared emitting light source, a detector of infrared light, and a support to position a test element relative to the light source and detector. As described for example in U.S. Pat. No. 4,420,566, such light source has been an incandescent lamp and the detector a PbS cell. These were positioned to detect IR radiation REFLECTED from the surface of a test element, inasmuch as the amount reflected changes if water or water-based serum is present. Thus, the apparatus serves as a drop detector, and can be used to detect pre-spotting, an undesirable event that occasionally occurs.

Although such apparatus has been very useful, the lamp has proven to have a relatively short life, and the components are relatively expensive. Known substitutes for the lamp and PbS cell are, respectively, an infrared (IR) light-emitting diode (LED) and a photo-sensitive transistor or photodiode. Further, these are less expensive with a longer life. However, when these are substituted into the analyzer described above for reflection detection, they prove to be too insensitive to be useful. More precisely, they are not capable of detecting from noise, the existence of a pre-spot, a needed function of such a drop detector. This is considered to be due to the wavelengths of light emitted by the LED not being strongly absorbed by water. Thus, this replacement for the drop detector already being used was initially discarded.

SUMMARY OF THE INVENTION

I have accidentally discovered that the sensitivity of such an IR light-emitting diode and a photo-sensitive transistor or photodiode are greatly increased, for water detection, if the two components are used to detect IR transmission, instead of reflection.

More specifically, as a result of this discovery, there is provided a method for detecting undesirable pre-spots at a dispense station in an analyzer by using an IR light-emitting diode and a photo-sensitive transistor or photodiode, comprising the steps of: a) positioning a test element on which liquid is to be dispensed in a predetermined amount at a prescribed time, in between said light-emitting diode and transistor or photodiode, b) detecting IR light that is transmitted only, by the test element, so that the sensitivity of the transistor or photodiode is enhanced, and c) comparing the amount of light transmitted against a baseline level to determine whether a pre-spot of liquid has been inadvertently dispensed prior to the dispensing of the predetermined, desired amount.

Accordingly, it is an advantageous feature of this invention that the less expensive and more reliable IR light-emitting diode and photo-transistor or photodiode can be used for pre-spot detection, even though their sensitivity is unsatisfactory when used as taught by the prior art.

Other advantageous features will become apparent upon reference to the following Description of the Preferred Embodiments, when read in light of the attached drawings.

BRIEF DESCRIPTION OF THE DRAWINGS

FIG. 5 is a flow chart of the logic used to program the method of the invention.

DESCRIPTION OF THE PREFERRED EMBODIMENTS

The invention is described as it is practiced with the preferred embodiments, featuring a particular preferred clinical analyzer and slide test elements. In addition, it is useful regardless of the construction of either the analyzer or the test elements, so long as a) the analyzer uses an infrared (IR) light-emitting diode and a photo-sensitive transistor or photodiode, and b) the test element will transmit IR light when wetted.

Figure 1:
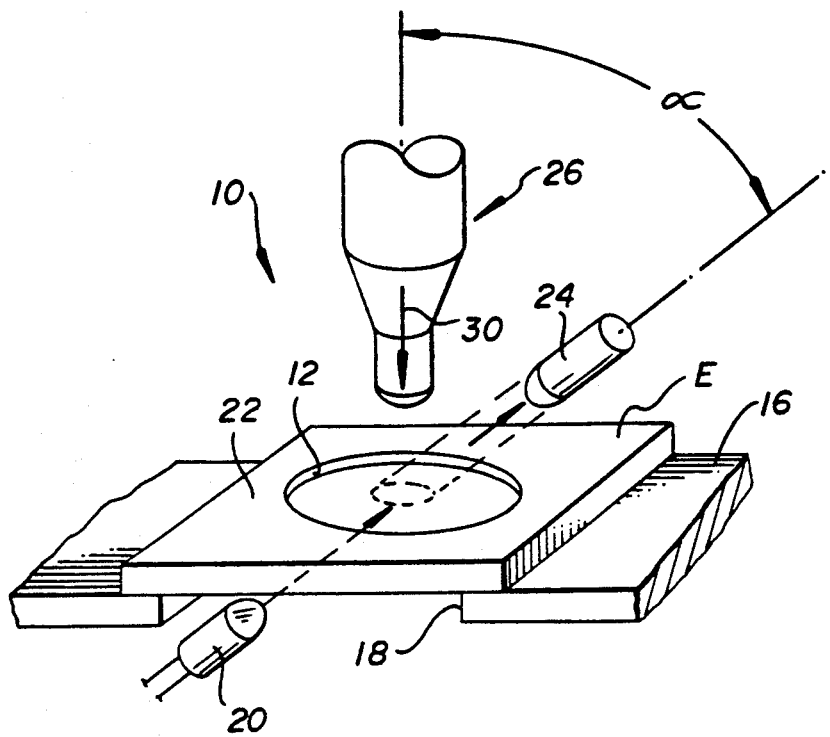
FIG. 1 is a fragmentary perspective view of apparatus useful in the practice of the invention, particularly at the dispensing station.

As shown in FIG. 1, the invention allows the wetting of a slide test element E to be detected at a dispensing station 10. Such a test element is preferably either the dried, slide elements available from Eastman Kodak Company under the trademark "Ektachem" slides, or the dried, slide elements available from Fuji Photo Film Co. under the tradename "DRyChem" slides. Further description of such elements is unnecessary, other than to point out that the element has an aperture 12 that allows a drop of liquid sample to be dispensed into the element, and is transparent enough through the center portion to transmit IR light, particularly when wet.

At station 10, a support surface 16 is provided to hold a test element in place during liquid dispensing. Any suitable restraining means (not shown) can ensure that element E is restrained in all three orthogonal directions, above an aperture 18 in surface 16. Positioned below aperture 18 is any IR-light-emitting diode 20, for example a GaAs or GaAlAs diode whose emission is centered at 935 and 890 nm, respectively, available from Optek Technology, Inc.

Adjacent to the opposite side 22 of element E, namely the side with opening 12, are the light-detector 24 and the sample dispenser 26. Detector 24 is any photo-sensitive transistor or photodiode, for exaple, an NPN silicon transistor available from Optek Technology, Inc., or a PIN or PN junction photodiode available, for example, from Optek Technology, Inc. under the tradenames OP 913SL or OP 900SL, respectively. Preferably, the centerline of the diode light emission distribution is aligned with the centerline of the detector distribution, and these centerlines are inclined at an angle "alpha" to the vertical axis and hence to the axis of dispenser 26. Angle "alpha" preferably is between about 40° and about 60° so as to position these optical components clear of the sample dispenser yet close to element E.

Regarding dispenser 26, any conventional dispenser can be used, for example, that available in the analyzers available from Eastman Kodak Co. under the trademark "Ektachem 700". Such a dispenser 26 includes a movable probe, not shown, on which is mounted a disposable tip 28. Pressure means (not shown) are effective to dispense an aliquot of sample in the direction of arrow 30, for example 10 μL, onto element E at aperture 12.

Figure 2:
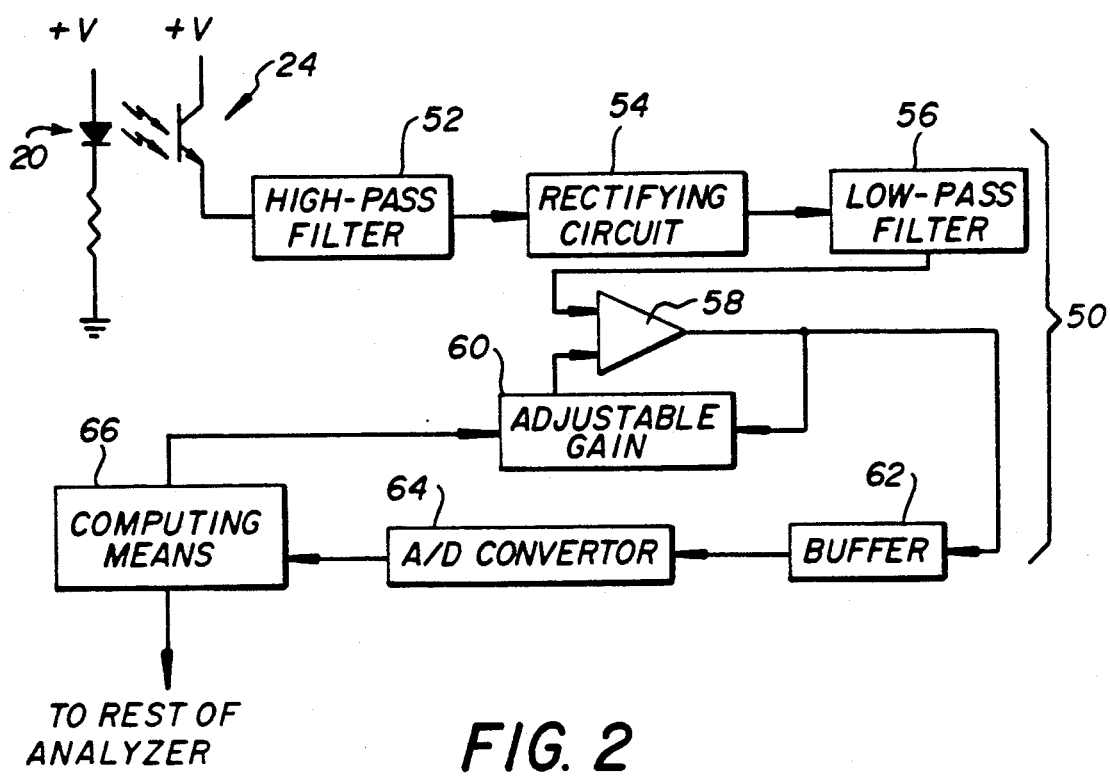
FIG. 2 is a schematic diagram of an electrical circuit useful in the practice of the invention.

Diode 20 and transistor 24 generate an electrical signal that can be used to sense the wetting of element E, using circuitry 40, FIG. 2. This circuitry 50 comprises a high-pass filter 52 to eliminate any DC component of the received square wave signal, a rectifying circuit 54 and a low-pass filter 56 that converts the square wave signal to a steady positive signal proportional to the amount of light detected by the photo-sensitive transistor or photodiode. An amplifier 58 is provided with an adjustable gain 60 to amplify the signal, a buffer 62 to convert the negativized signal out of amp 58 to a positive signal, and an A/D converted 64. All of these components are conventional, so that no details need be discussed. The resulting A/D counts are supplied to computing means 66, that in turn controls the analyzer.

In accord with one aspect of the invention, the aforedescribed apparatus is used to detect whether or not a preliminary spot of liquid, herein called a "pre-spot", of liquid has fallen or otherwise been dispensed onto element E at aperture 12. Such pre-spots are objectionable since they alter the chemical reaction that occurs when the desired aliquot is dispensed. Broadly, the method features the steps of positioning element E as shown, and reading the amount of IR light transmitted through the element up until the time for the prescribed dispensing of the desired aliquot of liquid. No fixed time for the "dispense time" is necessary, although the examples which follow show a time of 1 second following the onset of reading the IR transmission. It will be appreciated that enough read time is selected before the "dispense time" to ensure that all pre-spots, if any, will be detected. If during this read time, the amount of transmission deviates from a baseline value by more than a preselected threshold amount, then a pre-spot of liquid is present and the test is repeated. A preferred threshold amount to be exceeded before a "pre-spot" is announced is about +8% of the baseline value. Only IR light that is transmitted, is detected, since the apparatus is not suited for reflected IR light.

Figure 3:
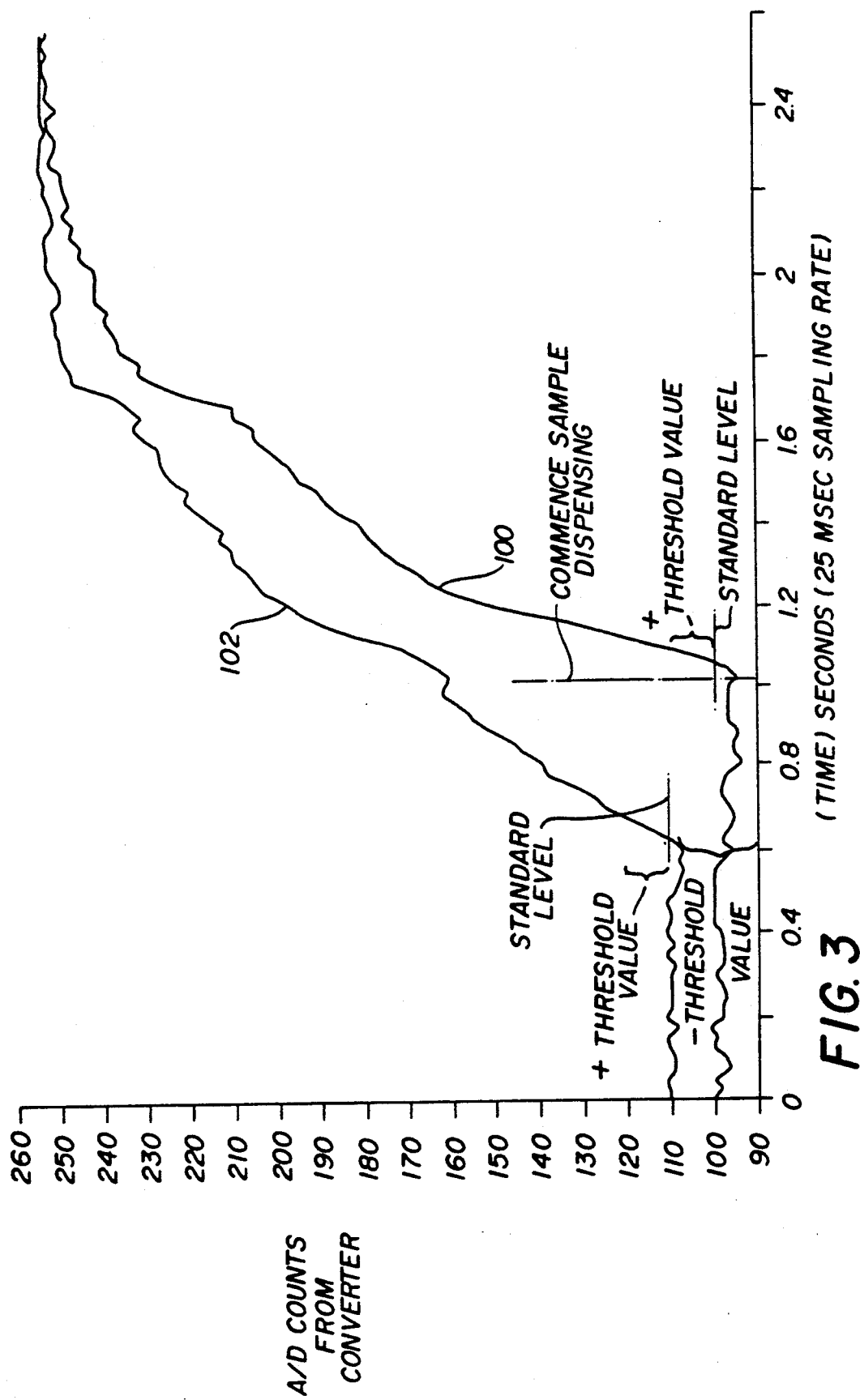
FIGS. 3–4 are plots of the amount of signal, or the rate of change of that signal, produced by the receipt by a transistor of IR light transmitted through a test element, either with or without a pre-spot.

FIG. 3 illustrates this method, wherein the simple change in the amount of the signal is enough to identify a pre-spot, using a calcium "Ektachem" slide. (In this test, as well as those of FIGS. 4 and 5, angle "alpha" was about 40°, LED 20 was about 12.3 mm below the plane of the undersurface of element E, and a photosensitive transistor 24 was about 6.4 mm above surface 22 of element E. Additionally, the LED was driven with a 2/3 duty cycle square wave at a frequency of about 833 Hz, the on-state collector current of the transistor was about 35 mA and the collector-emitter voltage was about 14.5 volts. In each illustration of pre-spots, the pre-spot was deliberately created by pre-dispensing a 3 μL pendant drop from the tip before the tip was seated above the element E. Then, when the tip was seated, the normal shock that occurred was sufficient to dislodge the 3 μL as a pre-spot. Visual confirmation was not needed.)

The analyzer was programmed to initiate the dispensing of 10 μL at about T=1.0 sec. Prior to this, at time T=0, a reading was taken, curve 100, of about 100 A/D counts, and this was assigned as the "baseline" value. Because there was no plus deviation greater than the preselected threshold value of 8 counts before T=1.0, the curve was interpreted as being normal, without any prespotting. However, when another identical test element (calcium) was subsequently positioned and curve 102 commenced, the results were different. (At time T=0, a "baseline" of 110 counts was ascertained.) Shortly before T=1.0 sec, the signal count rose to over 150, which was a difference of 40 that exceeded the threshold value of 8.8. Such increase is caused by the slide element being wetted with a pre-spot. Hence, this slide test element was labeled as having received a pre-spot, and was discarded.

Other chemistries with which the raw A/D count measurement is adequate, including $NH_3$ and theophylline.

Figure 4:
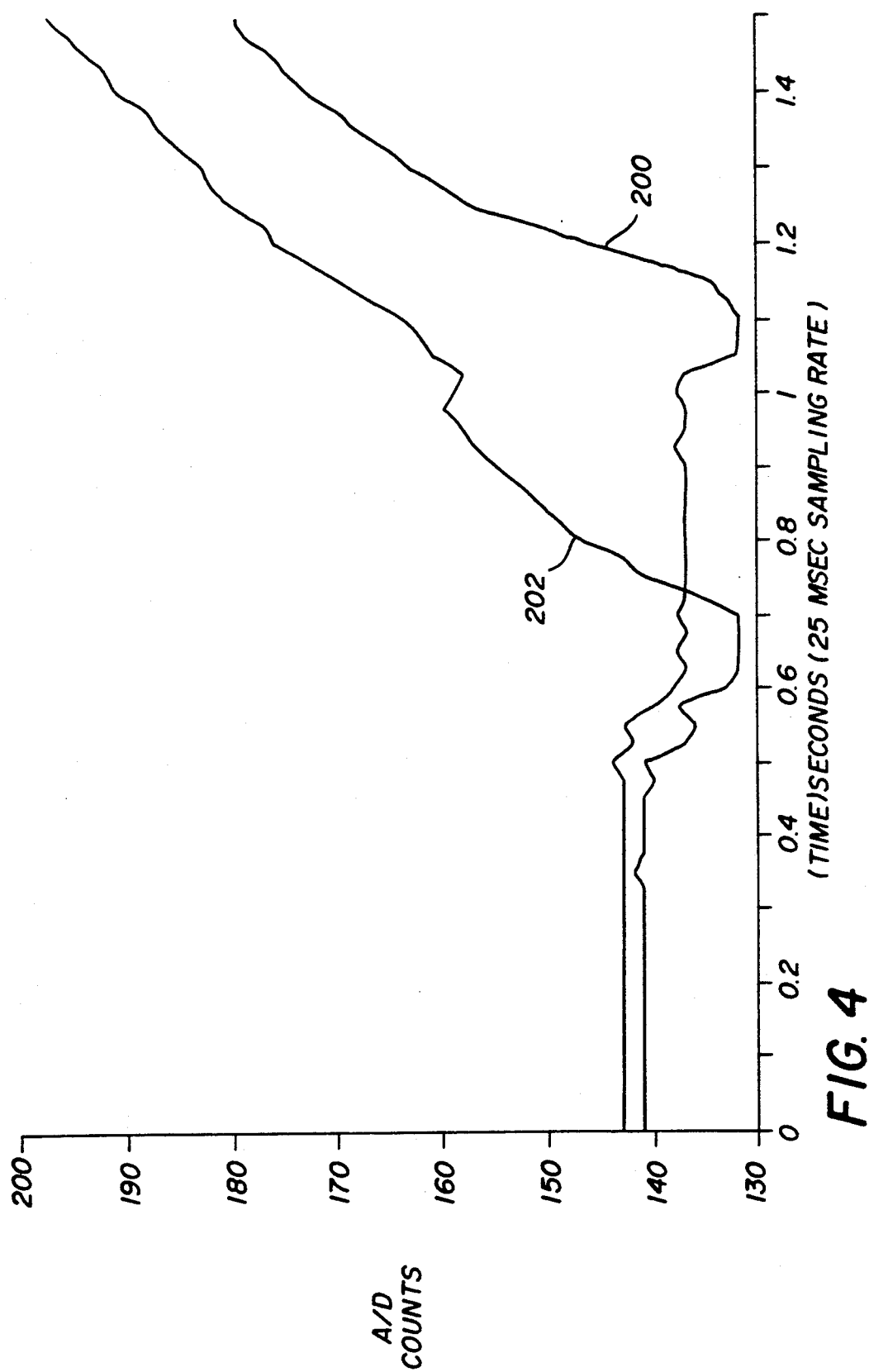

The process was repeated in the test shown in FIG. 4, except that the test elements were obtained from Eastman Kodak Co. under the trademark "Ektachem Total Protein", instead of calcium. Curve 200 was normal dispensing, whereas curve 202 was the curve that occurred with a pre-spot being dispensed at T=approximately 0.7 sec. In both cases, normal dispensing occurred at T=1 sec. (The dip in curve 200 at T=1.1 sec is believed to be due to the shadow created by the liquid beading up on the surface of element E before wetting occurs, due to the hydrophobic nature of the total protein chemistry.)

For curve 200, the baseline value was about 143, creating a threshold of +11.44. For curve 202, the baseline value was about 141, creating a threshold value of +11.28. This latter was exceeded before T=1.0, as the A/D count produced a deviation in excess of +15 at T=0.95 sec. (The unusual decrease in the first derivative at point A, for curve 200, which also occurred for curve 202, is attributable to the shadow of the dispensing tip. This shadow is preferably ignored by commanding the apparatus to only detect positive, and not negative, deviations from the baseline value.)

Similar results have been obtained when testing other "Ektachem" slide elements, e.g., albumin, cholesterol and the like.

The time for detecting whether the threshold has been exceeded can be the entire time between the time when baseline is set and the time when normal dispensing occurs (T=1.0 sec for the above examples.) However, since the A/D value does not decrease much once wetting occurs, the preferred reading time to ascertain whether the plus threshold has been exceeded is a one-time reading just prior to the normal dispense time, e.g., 50 to 100 millisec before.

It will be readily apparent that computing means 66 of FIG. 2 is preferred to carry out the process, particularly regarding the processing of the signal to measure its changes against a standard level and a threshold level. Conventionally, one or more of the microprocessors of the analyzer are used for this purpose. Any convenient program can be used, following the logic of the flow chart of FIG. 5. The first step, step 400, is to load a gain=1 into the auto gain register of gain 60, FIG. 2. This in turn provides a gain of 1 to the amplifier 58. The next several steps are used to ensure that the baseline signal produced by the A/D counts is not near the limits of detection, namely zero or 255. Specifically, step 402, an element E is positioned to receive patient liquid, and a baseline value of the IR transmitted is obtained, step 404, by taking and averaging 4 A/D readings. Such readings are preferably about 33 millisec apart, and can occur at T=0 in the context of the above examples. Next, the A/D average reading is queried, step 406, to determine if it is less than 50. If yes, step 408, the gain value of the auto gain register is doubled, and steps 404 and 406 are repeated. If no, then the average count is queried as to whether it exceeds 100, step 410. If yes, the gain is divided by 1.5, step 412, and that is used in the auto gain register (and amplifier 58), and steps 404 and 406 are again repeated. If no, the new average is retained in a register "X", step 414. Then, just prior to time T=normal dispense time, e.g., 50 to 100 millisec prior, four A/D readings are again taken and averaged, step 416, and the average is stored in register "Y". The difference between the values of register "Y" and "X" is calculated as a percent, step 418, and this percent is queried, step 420. If the percent change has exceeded +8% of the baseline value (the value in register "X"), then a pre-spot is "announced", step 422, the element E is discarded, and the procedure starts over at step 400. If the percent change is less than +8%, step 424, then there has been no pre-spot, and the analysis continues to completion, step 426.

Other threshold values besides 8% can be used. The 8% has been found to be particularly useful, however, since it is just less than the smallest increase that is produced by a pre-spot on total protein elements E, the slide elements that produce the smallest increase when pre-spotted. On the other hand, 8% is larger than deviations that are "noise" in the signal.

It is not necessary, although it is preferred, that the diode be opposite the side of the test element to which the sample dispenser is adjacent. That is, the positions of the diode and transistor shown in FIG. 1 can be reversed, and the method will still work. However, when the light beam transmission is so reversed, so as to be concurrent with the direction of flow of sample into element E, then the proportion of emitted light that is detectable is decreased, producing a lower signal-to-noise ratio. Hence, the preferred of the two choices is that shown in FIG. 1.

By comparison, the use of the diode and the transistor or photodiode in measuring IR light reflected from such test elements, failed to reliably detect a pre-spot due to the change or rate of change of the signal.

The invention has been described in detail with particular reference to certain preferred embodiments thereof, but it will be undestood that variations and modifications can be effected within the spirit and scope of the invention.

What is claimed is:

1. A method for detecting undesirable pre-spots at a dispense station in an analyzer by using an IR light-emitting diode and a photo-sensitive transistor or photodiode, comprising the steps of:
   a) positioning a test element on which liquid is to be dispensed in a predetermined amount at a prescribed time, in between said light-emitting diode and transistor or photodiode,
   b) detecting IR light that is transmitted only, by said test element, so that the sensitivity of said transistor or photodiode is enhanced, and
   c) comparing the amount of light transmitted against a baseline level of light transmitted to determine whether a pre-spot of liquid has been inadvertently dispensed prior to the dispensing of the predetermined, desired amount.

2. A method as defined in claim 1, wherein said dispense station includes a liquid-dispensing orifice, and wherein said light-emitting diode is disposed adjacent the side of a positioned test element that is opposite the side of the test element that is adjacent to said orifice, so that the IR light is emitted in a direction opposite to the flow of liquid in the positioned element and the detection of pre-spots is optimized.

3. A method as defined in claim 2, wherein said comparing step c) comprises comparing the change in the amount of IR-light transmitted against said baseline level to determine if a preselected threshold has been exceeded.

4. A method as defined in claim 3, wherein said threshold is about +8% of said baseline level.

5. A method as defined in claim 1, wherein said comparing step c) comprises comparing the change in the amount of IR-light transmitted against said baseline level to determine if a preselected threshold has been exceeded.

* * * * *